United States Patent

Both et al.

(10) Patent No.: US 6,911,567 B2
(45) Date of Patent: Jun. 28, 2005

(54) METHOD FOR PRODUCING GUERBET ALCOHOLS

(75) Inventors: Sabine Both, Duesseldorf (DE); Georg Fieg, Mettmann (DE); Erich Reuter, Duesseldorf (DE); Frank Bartschick, Neuss (DE); Bernhard Gutsche, Hilden (DE)

(73) Assignee: Cognis Deutschland and GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/380,978

(22) PCT Filed: Sep. 11, 2001

(86) PCT No.: PCT/EP01/10477

§ 371 (c)(1),
(2), (4) Date: Mar. 20, 2003

(87) PCT Pub. No.: WO02/24616

PCT Pub. Date: Mar. 28, 2002

(65) Prior Publication Data

US 2003/0181770 A1 Sep. 25, 2003

(30) Foreign Application Priority Data

Sep. 20, 2000 (DE) .......................... 100 46 433

(51) Int. Cl.$^7$ .......................... C07C 29/34; C07C 29/32
(52) U.S. Cl. ....................... 568/878; 568/876
(58) Field of Search .................. 568/878, 876

(56) References Cited

FOREIGN PATENT DOCUMENTS

WO    WO 91/04242    4/1991

OTHER PUBLICATIONS

H. Machemer, "Über die Guerbetsche Reaktion und ihre technische Bedeutung", Angew. Chem., 64, (1952), pp. 213–220.

*Primary Examiner*—Elvis O. Price
(74) *Attorney, Agent, or Firm*—Daniel S. Ortiz

(57) ABSTRACT

Guerbet alcohols of the formula (I)

$$CH_3(CH_2)_n CHR^1 CH_2 OH \qquad (I)$$

wherein $R^1$ is a linear alkyl radical having n-1 carbon atoms and n is a number of from 5 to 11 are produced by a process which comprises contacting a fatty alcohol of the formula (II)

$$R^2 OH \qquad (II)$$

wherein $R^2$ is a linear alkyl radical having from 6 to 12 carbon atoms with a carbonyl compound and an alkali metal hydroxide. The use of heavy metal catalysts usually associated with the production of Guerbet alcohols is avoided thereby reducing the potential for heavy metal pollution of the environment.

8 Claims, No Drawings

METHOD FOR PRODUCING GUERBET ALCOHOLS

BACKGROUND OF THE INVENTION

The invention relates to the field of cosmetic oil bodies or components and concerns an improved method for producing Guerbet alcohols without the use of heavy metal catalysts.

Guerbet alcohols represent primary alcohols which are branched in the 2-position and which are obtained by the condensation of linear fatty alcohols. The products are used predominantly as oil components for the production of cosmetic emulsions. The basic starting point for the production thereof is generally fatty alcohols which in a first step undergo self-condensation under the influence of strong bases and heavy metal compounds such as for example copper or zinc oxide. It is assumed that, under the reaction conditions, the alcohol is firstly dehydrated to form the aldehyde, the latter reacting with itself in an aldol condensation and the condensation product is then hydrated to form the alcohol. An overview in that respect is to be found for example in Angew. Chem. 64, 212 (1952).

There is, however, the disadvantage that the heavy metal catalysts have to be separated off again after the reaction is terminated in order to satisfy statutory requirements and to ensure that they do not cause irritations in the later use. Separation is generally effected by washing with subsequent distillation, in which respect the latter involves not inconsiderable product losses.

Accordingly the object of the present invention is to provide a method of producing Guerbet alcohols which, compared to the state of the art, operates more economically and with reduced environmental pollution. In particular, the invention seeks to avoid the use of heavy metal catalysts and simple distillative purification of the products should be guaranteed without expensive centrifugal washing.

DESCRIPTION OF THE INVENTION

The subject-matter of the invention is a method of producing Guerbet alcohols of the formula (I)

wherein $R^1$ represents a linear alkyl radical having n-1 carbon atoms and n represents numbers of between 5 and 11 carbon atoms, wherein fatty alcohols of the formula (II)

wherein $R^2$ represents linear alkyl radicals having between 6 and 12 carbon atoms are condensed in the presence of carbonyl compounds and alkali metal hydroxides.

It was surprisingly found that carbonyl compounds, especially fatty aldehydes, as alternatives to heavy metal compounds, also represent suitable catalysts for the Guerbet reaction, in particular if they are added at high temperatures. Accordingly a particular advantage of the method is that the condensation reaction is effected, with comparable levels of yield, in the absence of heavy metals, no washing is required in the finishing operation and thus there are also no longer any product losses.

Fatty Alcohols

Fatty alcohols, preferably those of the formula (II) in which $R^2$ represents an alkyl radical having between 8 and 10 carbon atoms are suitable for the condensation operation. Typical examples are hexanol, octanol, decanol, dodecanol and mixtures thereof.

Carbonyl Compounds

The carbonyl compounds which are used as catalysts are ketones, and in particular fatty aldehydes which are preferably in accordance with the formula (III)

wherein $R^3$ represents linear alkyl radicals having between 6 and 12 and in particular between 8 and 12 carbon atoms. Typical examples are hexanal, octanal, decanal, dodecanal and mixtures thereof. It has proven to be particularly advantageous to use fatty alcohols and fatty aldehydes with the same alkyl radical. Usually the carbonyl compounds in general and the fatty aldehydes in particular are used in amounts of between 0.2 and 50, preferably between 1 and 25 and in particular between 3 and 10 mol %, with respect to the fatty alcohols.

Condensation

The condensation reaction can be performed in per se known manner, that is to say the fatty alcohols, together with the bases, are heated to temperatures in the range of between 200 and 250, preferably between 210 and 240° C. The carbonyl compounds can then be added at a temperature of between 200 and 250° C. to the mixture of fatty alcohols and alkali metal hydroxide. It has proven to be advantageous, however, for the addition operation to be implemented at higher temperatures, that is to say between 210 and 240° C. The speed of addition also has an influence on the condensation reaction. Typical times are times of between 0.1 and 10 hours, having regard to the reaction speed and the yields, however, the recommendation is between 10 and 60 minutes. The amount of alkali metal hydroxides can be between 1 and 10, preferably between 3 and 5 mol % with respect to the fatty alcohols. Preferably at least 40% by weight of sodium hydroxide or in particular potassium hydroxide lye is used. At any event, to displace the reaction equilibrium onto the product side it is recommended that the condensation water be continuously distilled off. As organic material is easily entrained in that case it has proven worthwhile to use a dephiegmator, by means of which the organic phase is separated off and can be recycled into the starting material. The work-up procedure which now manages without a washing step then involves simple distillation. This affords fewer product losses and a lower level of waste water pollution.

EXAMPLE 1

1000 g (6.3 moles) of decanol (95% by weight) was put in a stirring apparatus comprising a flask, a heating-mantle member, a dephlegmator, a Liebig condenser, a nitrogen transfer device and a double-stroke piston pump, mixed at 200° C. with 22.5 g (0.22 mol) of 45% by weight potassium hydroxide solution and heated to 215° C. The water which occurred upon heating was continuously distilled off. Then 29.6 g of decanal (corresponding to 3 mol % with respect to decanol) was meteredly added by way of the pump within 60 minutes and in that operation the temperature raised to 240° C. The distilled organic phase was fed to the reaction mixture after phase separation. The reaction was terminated after 6 hours. A GC analysis of the product mixture showed that 76% by weight of 2-octyldodecanol was produced; in addition the reaction mixture contained 6% by weight of timers, 14% by weight of unreacted monomer alcohol and 4% by weight of mixed Guerbet alcohols consisting of $C_{18}$- and $C_{22}$-Guerbet alcohols. Purification of the product was effected distillatively, the unreacted decanol was removed as a first running and was reintroduced into the reaction mixture; the residue that remained was the higher-molecular constituents.

EXAMPLE 2

Similarly to Example 1 1000 g (6.3 mol) of decanol was mixed with 22.5 (0.22 mol) of potassium hydroxide solution and 29.6 g of decanal and heated to 240° C. The water produced in the heating operation was continuously distilled off and the distilled organic phase fed to the reaction mixture after phase separation. The reaction was terminated after 6 hours. A GC analysis of the product mixture showed that 43% by weight of 2-octyldodecanol was produced; in addition the reaction mixture contained 2% by weight of trimers, 53% by weight of unreacted monomer alcohol and 2% by weight of mixed Guerbet alcohols consisting of $C_{18}$- and $C_{22}$-Guerbet alcohols.

What is claimed is:

1. A method for producing a Guerbet alcohol of the formula (I)

$$CH_3(CH_2)_n CHR^1 CH_2 OH \qquad (I)$$

wherein $R^1$ is a linear alkyl radical having n-1 carbon atoms and n is a number of from 5 to 11 comprising contacting a fatty alcohol of the formula (II)

$$R^2 OH \qquad (II)$$

wherein $R^2$ is a linear alkyl radical having from 6 to 12 carbon atoms with a carbonyl compound and an alkali metal hydroxide, and wherein the carbonyl compound is continuosly added to a mixture of fattyalcohols and alkali metal hydroxide over a period of from 0.1 to 10 hours and at a temperature of between 200° C. and 250° C.

2. The method of claim 1 wherein $R^2$ is an alkyl radical having from 8 to 10 carbons.

3. The method of claim 1 wherein the carbonyl compound is a fatty aldehyde.

4. The method of claim 3 wherein the fatty aldehyde is a compound of the formula (III)

$$R^3 CHO \qquad (III)$$

wherein $R^3$ is a linear alkyl radical having from 6 to 12 carbon atoms.

5. The method of claim 1 wherein the amount of the carbonyl compound is from 0.2 to 50 mole % with respect to the fatty alcohol.

6. The method of claim 1 wherein the amount of the alkali metal hydroxide is from 1 and 10 mole % with respect to the fatty alcohol.

7. The method of claim 1 further comprising the step of purifying the guerbet alcohol by distillation.

8. A method for producing a Guerbet alcohol of the formula (I)

$$CH_3(CH_2)_n CHR^1 CH_2 OH \qquad (I)$$

wherein $R^1$ is a linear alkyl radical having n-1 carbon atoms and n is a number of from 5 to 11 comprising contacting a fatty alcohol of the formula (II)

$$R^2 OH \qquad (II)$$

wherein $R^2$ is a linear alkyl radical having from 6 to 12 carbon atoms with a carbonyl compound in a reaction mixture wherein the carbonyl compound is continuously added to the reaction mixture, maintained at a temperature of from about 210° C. to about 250° C. a period of from 0.1 to 10 hours.

* * * * *